(12) United States Patent
Barrett et al.

(10) Patent No.: US 8,517,968 B2
(45) Date of Patent: Aug. 27, 2013

(54) SHROUDED SENSOR CLIP ASSEMBLY AND BLOOD CHAMBER FOR AN OPTICAL BLOOD MONITORING SYSTEM

(75) Inventors: Louis L. Barrett, West Point, UT (US); Perry N. Law, Centerville, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 129 days.

(21) Appl. No.: 13/034,788

(22) Filed: Feb. 25, 2011

(65) Prior Publication Data

US 2012/0220914 A1    Aug. 30, 2012

(51) Int. Cl.
*A61M 37/00* (2006.01)
*G01N 33/48* (2006.01)

(52) U.S. Cl.
USPC ........... 604/6.09; 604/4.01; 604/5.04; 356/40

(58) Field of Classification Search
USPC .......... 604/4.01, 5.01, 5.04, 6.09; 356/39–40
See application file for complete search history.

(56) References Cited

U.S. PATENT DOCUMENTS

| | | | |
|---|---|---|---|
| 3,580,683 A | 5/1971 | Schulkind | |
| 3,728,032 A | 4/1973 | Noll | |
| 3,740,156 A | 6/1973 | Heigl et al. | |
| 4,243,883 A | 1/1981 | Schwarzmann | |
| 4,784,768 A | 11/1988 | Mathieu | |
| 5,231,464 A | 7/1993 | Ichimura et al. | |
| 5,247,434 A | 9/1993 | Peterson et al. | |
| 5,312,535 A | 5/1994 | Waska et al. | |
| 5,351,686 A | 10/1994 | Steuer et al. | |
| 5,366,630 A | 11/1994 | Chevallet | |
| 5,372,136 A | 12/1994 | Steuer et al. | |
| 5,456,253 A | 10/1995 | Steuer et al. | |
| 5,670,050 A | 9/1997 | Brose et al. | |
| 5,674,390 A | 10/1997 | Matthews et al. | |
| 5,730,712 A | 3/1998 | Falkvall et al. | |
| 5,762,805 A | 6/1998 | Truitt et al. | |
| 6,069,687 A | 5/2000 | Briggs | |
| 6,090,061 A | 7/2000 | Steuer et al. | |
| 6,284,131 B1 | 9/2001 | Hogard et al. | |
| 6,284,142 B1 | 9/2001 | Muller | |
| 6,746,415 B1 | 6/2004 | Steuer et al. | |
| 7,671,974 B2 | 3/2010 | O'Mahony et al. | |
| 2001/0016699 A1 | 8/2001 | Burbank et al. | |

(Continued)

FOREIGN PATENT DOCUMENTS

| EP | 0 274 178 A1 | 7/1988 |
|---|---|---|
| EP | 467805 A1 | 1/1992 |

(Continued)

OTHER PUBLICATIONS

International Search Report PCT/US2012/026637 (Jun. 6, 2012).

(Continued)

*Primary Examiner* — Leslie Deak
(74) *Attorney, Agent, or Firm* — Leydig, Voit & Mayer, Ltd.

(57) ABSTRACT

An optical blood monitoring system includes a sensor clip assembly and a blood chamber. The blood chamber has an internal flow cavity for extracorporeal blood flow and viewing lenses to enable the sensor clip assembly to monitor the blood when it is mounted on the blood chamber. The sensor clip assembly includes an annular shroud surrounding the LED emitters and another annular shroud surrounding the photodetectors, both for the purpose of blocking ambient light and limiting light piping. The blood chamber includes separate, distinct shroud mating surfaces to engage the shrouds on the sensor clip assembly.

41 Claims, 10 Drawing Sheets

(56) References Cited

U.S. PATENT DOCUMENTS

| | | |
|---|---|---|
| 2001/0021817 A1 | 9/2001 | Brugger et al. |
| 2001/0037079 A1 | 11/2001 | Burbank et al. |
| 2001/0041892 A1 | 11/2001 | Burbank et al. |
| 2002/0103453 A1 | 8/2002 | Burbank et al. |
| 2002/0147423 A1 | 10/2002 | Burbank et al. |
| 2003/0009123 A1 | 1/2003 | Brugger et al. |
| 2003/0097087 A1 | 5/2003 | Gura |
| 2003/0143116 A1 | 7/2003 | Zheng et al. |
| 2003/0210390 A1 | 11/2003 | O'Mahony et al. |
| 2005/0094127 A1 | 5/2005 | O'Mahony et al. |
| 2006/0036185 A1 | 2/2006 | Lewicke et al. |
| 2010/0110416 A1 | 5/2010 | Barrett et al. |
| 2011/0004082 A1 | 1/2011 | Poeze et al. |

FOREIGN PATENT DOCUMENTS

| | | |
|---|---|---|
| EP | 0 990 444 A2 | 4/2000 |
| GB | 1 583 023 | 1/1981 |
| WO | WO 93/06774 A1 | 4/1993 |
| WO | WO 93/06456 A1 | 9/1997 |
| WO | WO 00/33053 | 6/2000 |
| WO | WO 01/93944 A1 | 12/2001 |

OTHER PUBLICATIONS

Written Opinion of PCT/US2012/026637 (Jun. 6, 2012).
Blood Chamber 2001—Admitted Prior Art.
CL Photo 2000—Admitted Prior Art.
Blood Chamber Instruction Sheet 2001—Admitted Prior Art.
U.S. Appl. No. 12/876,5872, filed Sep. 7, 2010.
U.S. Appl. No. 13/405,148, filed Feb. 24, 2012.
Sacker-Berstein, Jonathan D., MD., et al., "How Should Diuretic-Refractory Volume-Overloaded Heat Failure Patients Be Managed?", *The Journal of Invasive Cardiology*, vol. 15, No. 10 (Oct. 2003), pp. 585-590, retrieved from http://www.medscape.com/viewarticle/463509_print on Mar. 11, 2013 pp. 1-11.
Jaski, Brian E. MD., "Peripherally Inserted Veno-Venous Ultrafiltration for Rapid Treatment of Volume Overloaded Patients", *Journal of Cardiac Failure*, vol. 9., No. 3 *Jun. 2003), pp. 227-231.

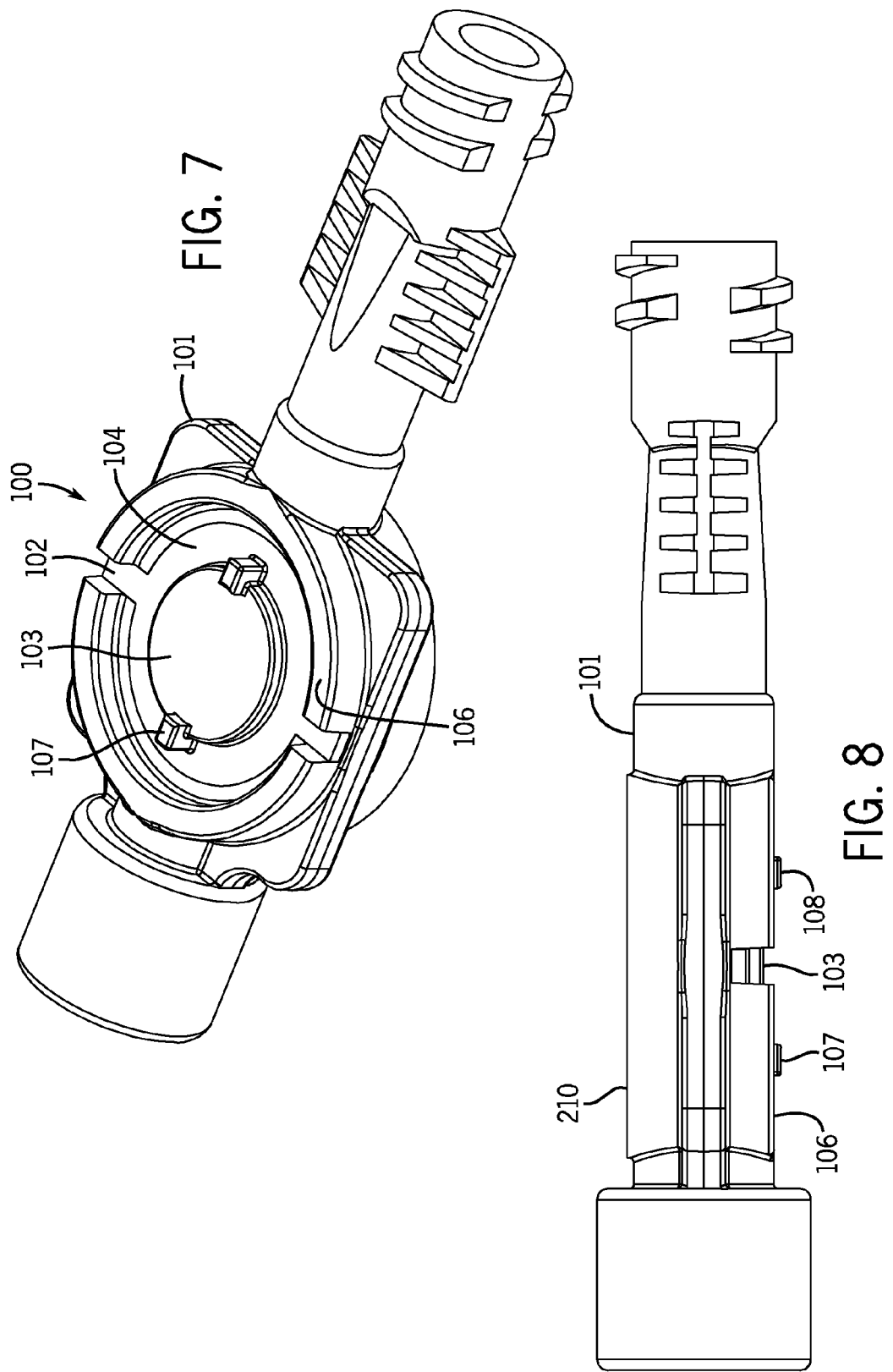

SHROUDED SENSOR CLIP ASSEMBLY AND BLOOD CHAMBER FOR AN OPTICAL BLOOD MONITORING SYSTEM

FIELD OF THE INVENTION

The invention relates to optical blood monitoring systems used to monitor extracorporeal patient blood flow and take real-time measurement of hematocrit, oxygen saturation levels and/or other blood constituents. The invention is particularly directed to improving the physical interface between the sensor clip assembly and the mating, single-use blood chamber.

BACKGROUND

The type of blood monitoring systems to which the invention pertains has been widely used to monitor a patient's hematocrit and oxygen saturation levels during conventional hemodialysis treatments. Patients with kidney failure or partial kidney failure typically undergo hemodialysis treatment in order to remove toxins and excess fluids from their blood. To do this, blood is taken from a patient through an intake needle or catheter which draws blood from an artery or vein located in a specifically accepted access location (for example, a shunt surgically placed in an arm, thigh, subclavian, etc.). The needle or catheter is connected to extracorporeal tubing that is fed to a peristaltic pump and then to a dialyzer that cleans the blood and removes excess water. The cleaned blood is then returned to the patient through additional extracorporeal tubing and another needle or catheter. Sometimes, a heparin drip is located in the hemodialysis loop to prevent the blood from coagulating. By way of background, as the drawn blood passes through the dialyzer, it travels in straw-like tubes within the dialyzer which serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration. Dialysate containing the removed toxins and excess fluids is disposed of as waste. The red cells remain in the straw-like tubes and their volume count is unaffected by the process.

It is known in the art to use an optical blood monitoring system during hemodialysis, such as the CRIT-LINE® monitoring system sold by the assignee of this application. The current CRIT-LINE® blood monitoring system uses optical techniques to non-invasively measure in real-time the hematocrit and the oxygen saturation level of blood flowing through a hemodialysis system or other systems involving extracorporeal blood flow. When the CRIT-LINE® system is used with conventional hemodialysis systems, a sterile, single-use blood chamber is usually attached in-line to the extracorporeal tubing on the arterial side of the dialyzer.

In general, blood chambers along with the tube set and dialyzer are replaced for each patient and the blood chamber is intended for a single use. The blood chamber provides an internal blood flow cavity, a substantially flat viewing region and two viewing lenses. Blood chambers commonly used are molded from clear, medical-grade polycarbonate. Typically, one of the viewing lenses is integrally molded with the body of the polycarbonate blood chamber, and the other viewing lens is molded into a separate lens body that is sonically welded or otherwise fixed to the chamber body. Alternatively, both lenses are molded into separate lens bodies that may be welded or otherwise affixed into place on the chamber body.

LED emitters and photodetectors for the optical blood monitor are clipped into place onto the blood chamber over the lenses. Multiple wavelengths of light may be directed through the blood chamber and the patient's blood flowing through the chamber with a photodetector detecting the resulting intensity of each wavelength. The preferred wavelengths to measure hematocrit are about 810 nm (e.g. 829 nm), which is substantially isobestic for red blood cells, and about 1300 nm, which is substantially isobestic for water. A ratiometric technique implemented in the CRIT-LINE® controller, substantially as disclosed in U.S. Pat. No. 5,372,136 entitled "System and Method for Non-Invasive Hematocrit Monitoring", which issued on Dec. 13, 1999 and is assigned to the assignee of the present application, uses this information to calculate the patient's hematocrit value in real-time. The hematocrit value, as is widely used in the art, is the percentage determined by dividing the volume of the red blood cells in a given whole blood sample by the overall volume of the blood sample.

In a clinical setting, the actual percentage change in blood volume occurring during hemodialysis can be determined, in real-time, from the change in the measured hematocrit. Thus, an optical blood monitor, such as the CRIT-LINE® monitor, is able to non-invasively monitor not only the patient's hematocrit level but also the change in the patient's blood volume in real-time during a hemodialysis treatment session. The ability to monitor real-time change in blood volume helps facilitate safe, effective hemodialysis.

The mathematical ratiometric model for determining the hematocrit (HCT) value can be represented by the following equation:

$$HCT = f\left[\frac{\ln\left(\frac{i_{\lambda 2}}{I_{0-\lambda 2}}\right)}{\ln\left(\frac{i_{\lambda 1}}{I_{0-\lambda 1}}\right)}\right] \quad \text{Eq. (1)}$$

where $i_{\lambda 2}$ is the infrared light intensity detected by the photoreceiver at about 810 nm, $i_{\lambda 1}$ is the infrared intensity detected at 1300 nm and $I_{0-\lambda 2}$ and $I_{0-\lambda 1}$ are constants representing the infrared light intensity incident on the blood accounting for losses through the blood chamber. The function $f[\ ]$ is a mathematical function which has been determined based on experimental data to yield the hematocrit value. Preferably, the function $f[\ ]$ in the above Equation (1) is a relatively simply polynomial, e.g. a second order polynomial. The above Equation (1) holds true only if the distance traveled by the infrared light radiation from the LED emitters to the photodetectors at both wavelengths are constant distances and preferably the same distance The preferred wavelengths to measure oxygen saturation level are about 810 nm and about 660 nm. The mathematical ratiometric model for determining oxygen saturation level (SAT) can be represented by the following equation:

$$SAT = g\left[\frac{\ln\left(\frac{i_{\lambda 3}}{I_{0-\lambda 3}}\right)}{\ln\left(\frac{i_{\lambda 1}}{I_{0-\lambda 1}}\right)}\right] \quad \text{Eq. (2)}$$

where $i_{\lambda 3}$ is the light intensity of the photoreceiver at 660 nm, $i_{\lambda 1}$ is the detected intensity at 810 nm and $I_{0-\lambda 3}$ and $I_{0-\lambda 1}$ are constants representing the intensity incident on the blood accounting for losses through the blood chamber. The function g[ ] is a mathematical function determined based on experimental data to yield the oxygen saturation level, again preferably a second order polynomial. Also, like Equation (1) for the hematocrit calculation, Equation (2) for the oxygen saturation level calculation holds true only if the distance traveled by the visible and infrared light from the respective LED emitter to the respective detector at both the 660 nm and 810 nm wavelengths are constant distances and preferably the same distance.

In the art, the LED emitters and the photodetectors are mounted on a sensor clip assembly. For accuracy of the system, it is important that the LED photoemitters and the photodetectors be located in a predetermined position and orientation each time the sensor clip assembly is clipped into place over the blood chamber. The optical monitor is in fact calibrated for the specific dimensions of the blood chamber and the specific position and orientation of the sensor clip assembly with respect to the blood chamber. For this purpose, in the prior art, the heads of the sensor clips are designed to mate in a fixed orientation with non-circular, raised and stepped rims surrounding the viewing lenses on the blood chamber (e.g. double-D configuration). More specifically, the heads on both sides of the sensor clip assembly are formed in a non-circular shape, e.g. a double-D configuration, which matches the corresponding non-circular shape of the raised, stepped rims surrounding the viewing lenses on the blood chamber so that the sensor clip heads fit on the blood chamber in a fixed orientation and are prevented from rotating relative to the blood chamber. While the double-D configuration has proven to work well, one drawback of the design is the additional amount of medical grade polycarbonate material that is required to manufacture the raised, stepped rims. In order to reduce the cost of manufacturing the blood chambers which are single-use, disposable medical devices, it is desirable to reduce the amount of medical grade polycarbonate in the blood chambers.

If not addressed properly, stray ambient light and light piping through the blood chamber can cause serious inaccuracies in the measured hematocrit and/or oxygen saturation levels. Sophisticated signal processing techniques have been used in the art to remedy most of the issues pertaining to ambient light. In addition, prior art blood chambers are molded with a moat around a relatively thin, flat viewing area in the blood flow cavity between the viewing lenses. This internal moat within the blood flow cavity fills with blood and blocks light from the silicon and gallium indium arsenide photodetectors on the sensor clip assembly unless the light propagates on a direct path from the respective LED emitter, through the blood in the blood flow cavity, to the respective photodetector. The effectiveness of the moat depends on many factors including the patient's hematocrit level and the wavelength spectrum of the light that is sought to be blocked from the photodetectors. In practice, the above-mentioned signal processing techniques have been found necessary to cope with most ambient light issues, whereas the moat has been found useful to reduce inaccuracies due to light piping in most circumstances. Co-pending patent application Ser. No. 12/876,572, entitled "Blood Chamber for an Optical Blood Monitoring System", by Barrett et al, assigned to assignee of the present application and incorporated herein by reference, discloses the use of an opaque chamber body in order to prevent inaccuracies when measuring oxygen saturation levels due to light ducting which can occur at low oxygen saturation levels and low hematocrit levels. Both the use of the moat and the opaque chamber body physically block piped and/or ambient light. The present invention is directed to providing another way to physically block ambient light from the photodetectors.

SUMMARY OF THE INVENTION

The invention pertains to the use of an optical blood monitoring system having a sensor clip assembly and a blood chamber designed to physically block ambient light from the photodetectors on the sensor clip assembly. The sensor clip assembly includes an emitter subassembly to which the LED photoemitters are mounted and a photo detector subassembly to which the photo detectors are mounted. As known in the art, the emitter subassembly and the detector subassembly are arranged to face one another and to be clipped onto a blood chamber when the monitoring system is in use. A first aspect of the invention is directed to the use of a shroud on the emitter subassembly and another shroud on the detector subassembly to prevent ambient light from entering the blood chamber. In the preferred of the invention, the heads on the sensor clip each include a shroud in the form of circular a wall that encircles the LED emitters and photodetectors, respectively. It is known in art that the LED photoemitters direct light through a diffusing lens mounted on the head of the emitter subassembly, and that the photodetectors receive light through a diffusing lens mounted on the head of the detector subassembly. The purpose is to distribute light energy across the volume of blood in the lens areas of the blood chamber to avoid hot spots of concentrated light from the emitters for consistency in calibrations. In accordance with the invention, it is preferred that the emitter shroud be spaced apart from the diffusing lens related to the emitter subassembly and also extend away from the emitter subassembly toward the detector subassembly to a distance beyond the emitter diffusing lens. Similarly, it is preferred that the detector shroud be spaced apart from the diffusing lens related to the detector subassembly and also that the detector shroud extend away from the detector subassembly to a distance beyond the detector diffusing lens. Thus, when the sensor clip is clipped on the blood chamber, the shrouds effectively surround the viewing lenses on both sides of the blood chamber and block ambient light. The incident angle of light rays from the LED emitters into the wall of the blood chamber is also limited by the shroud geometry thereby minimizing possible light piping.

Another aspect of the invention is directed to the design of the blood chamber to enable the use of the shrouded sensor clip assembly. In this regard, the blood chamber includes a first and second exterior side each having a viewing lens and a separate, distinct shroud mating surface located circumferentially around the viewing lens. Preferably, on one exterior surface of the blood chamber, the first viewing lens is raised above the circumferential shroud mating surface such that a sunken annular well is formed around the raised viewing lens. The floor of the sunken annular well corresponds to the shroud mating surface on that side of the blood chamber. It is preferred that the shrouds on the clip assembly when mounted on the blood chamber substantially fill the area of the floor of the sunken annular well in order to maximize the amount of ambient light blocked by the shroud. It is preferred that the other exterior surface of the blood chamber include an upstanding wall that surrounds the second viewing lens and separates the second viewing lens from the shroud mating surface on that side of the blood chamber. In this way, an annular well is formed around the second viewing lens, although this annular well is preferably at substantially the same depth as the viewing lens on that side of the blood chamber. Again, the floor of the annular well corresponds to the shroud mating surface on the exterior side of the blood chamber, and has dimensions substantially the same as the dimensions of the floor of the sunken annular well on the other side of the blood chamber so that the shroud will fill the surface area of the floor of the well.

The improved design with the shrouds on the sensor clip assembly not only reduces the influx of ambient light, but also enables the use of less molded material (e.g. medial grade polycarbonate) in the manufacture of the blood chamber over previous designs. As mentioned, prior art blood chambers have non-circular (e.g. double-D configuration), raised, stepped rims surrounding the viewing lenses to fix the relative position and orientation of the LED emitters and photodetectors with respect to the blood chamber. The present invention eliminates the need for such a non-circular, raised, stepped rims surrounding the viewing lenses. Instead, the blood chamber preferably has one or more anti-rotation tabs to fix the position of the sensor clip assembly and prevent rotation relative to the blood chamber. In one embodiment, a pair of extending tabs is formed on an exterior surface on one side of the blood chamber. The anti-rotation tabs may take on any reasonable geometric shape, but are designed to inter-engage with the shroud. In the preferred embodiment, the shrouds on the sensor clip assembly contain mating slots which are shaped to receive the anti-rotation tabs. The engagement of the tabs, fixes the orientation of the sensor clip assembly with respect to the blood chamber. The shroud with the tab receiving slot eliminates the need for the non-circular raised, stepped rims surrounding the viewing lenses on the blood chamber, and therefore reduces the amount of molded material needed to manufacture the blood chamber. One skilled in the art will understand that placing anti-rotation tabs on the shrouds and including mating detents or slots on the blood chamber, while not preferred, may be a suitable alternative to carry out this aspect of the invention. Either arrangement is likely to reduce the amount of material needed to mold the blood chamber.

Other advantages and features of the invention may be apparent to those skilled in the art upon reviewing the drawings and the following description thereof.

BRIEF DESCRIPTION OF THE DRAWINGS

Prior Art

Embodiments of the Invention

Figure 6:
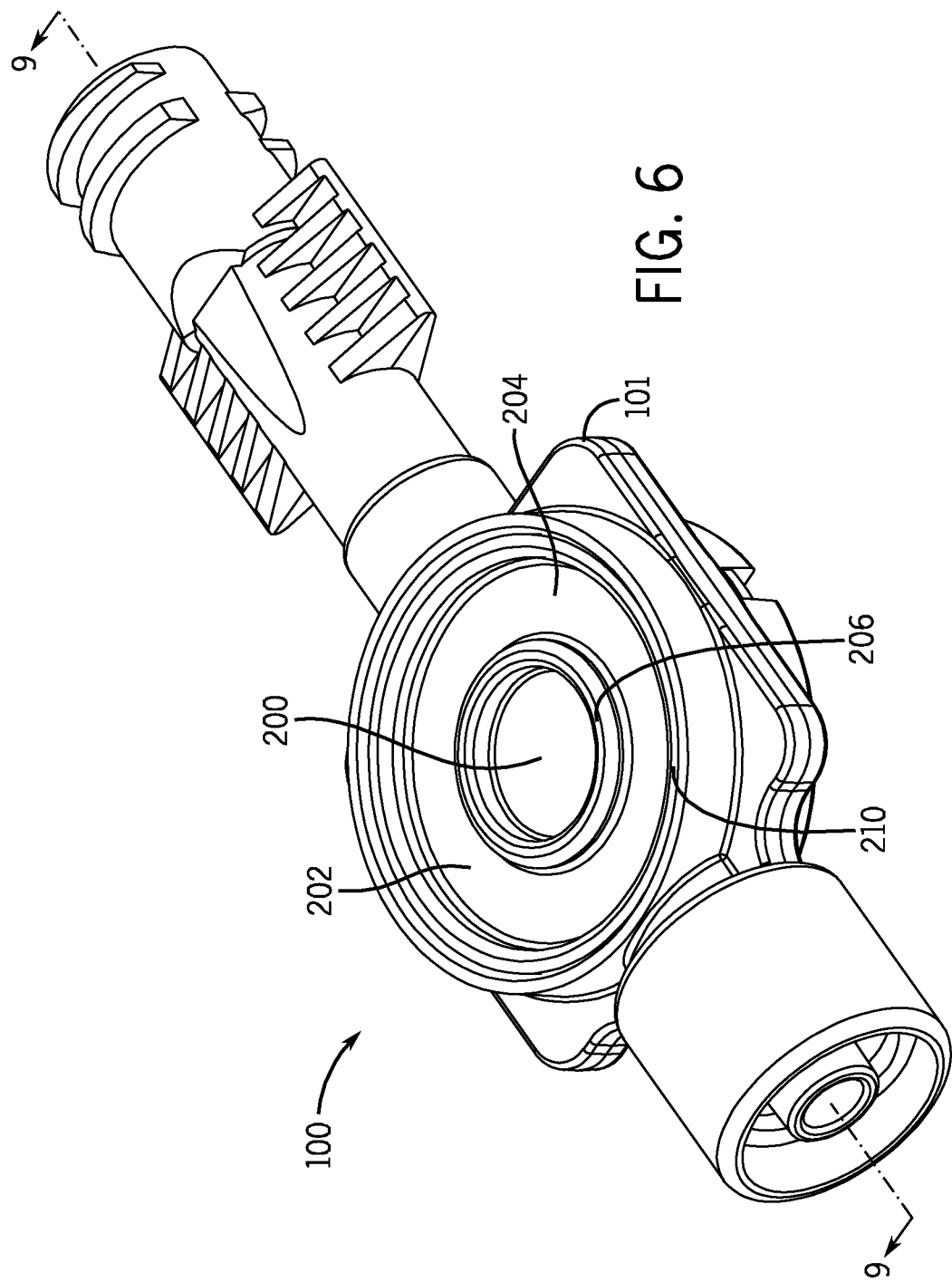

FIG. 6 is a perspective view of one side of a blood chamber constructed in accordance with an embodiment of the invention.

FIG. 7 is a perspective view of the other side of the blood chamber shown in FIG. 6.

FIG. 8 is a front elevation view of the blood chamber shown in FIG. 6.

Figure 9:
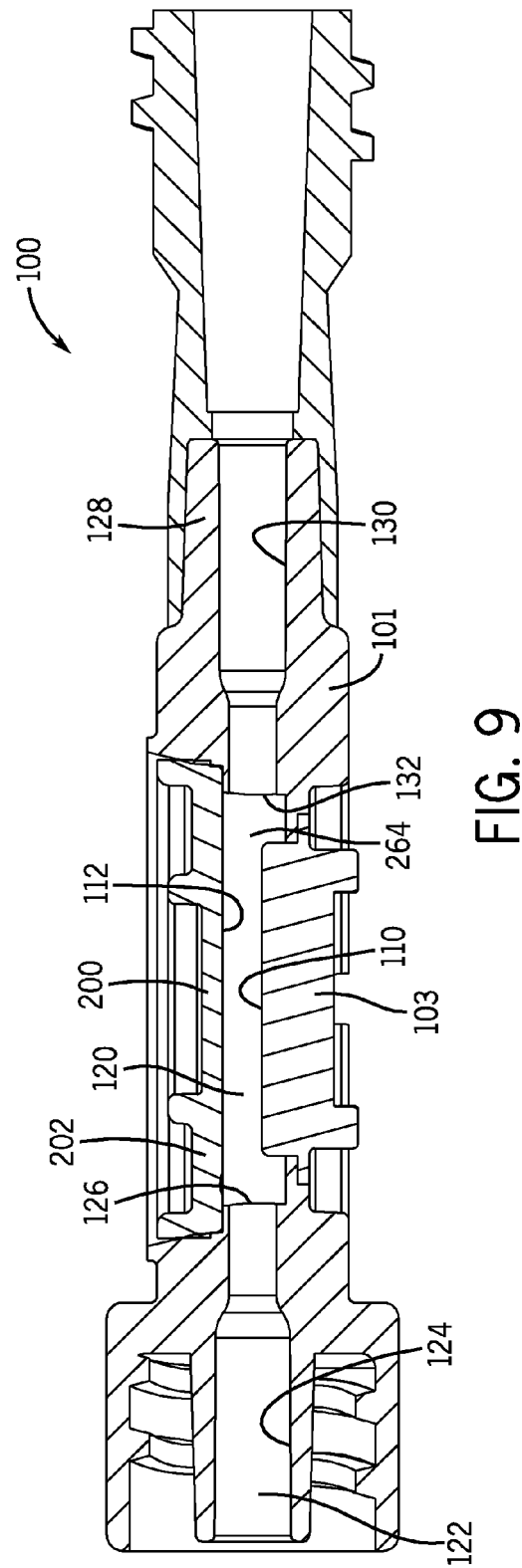

FIG. 9 is a is a longitudinal sectional view taken along line 9-9 in FIG. 6.

Figure 10:
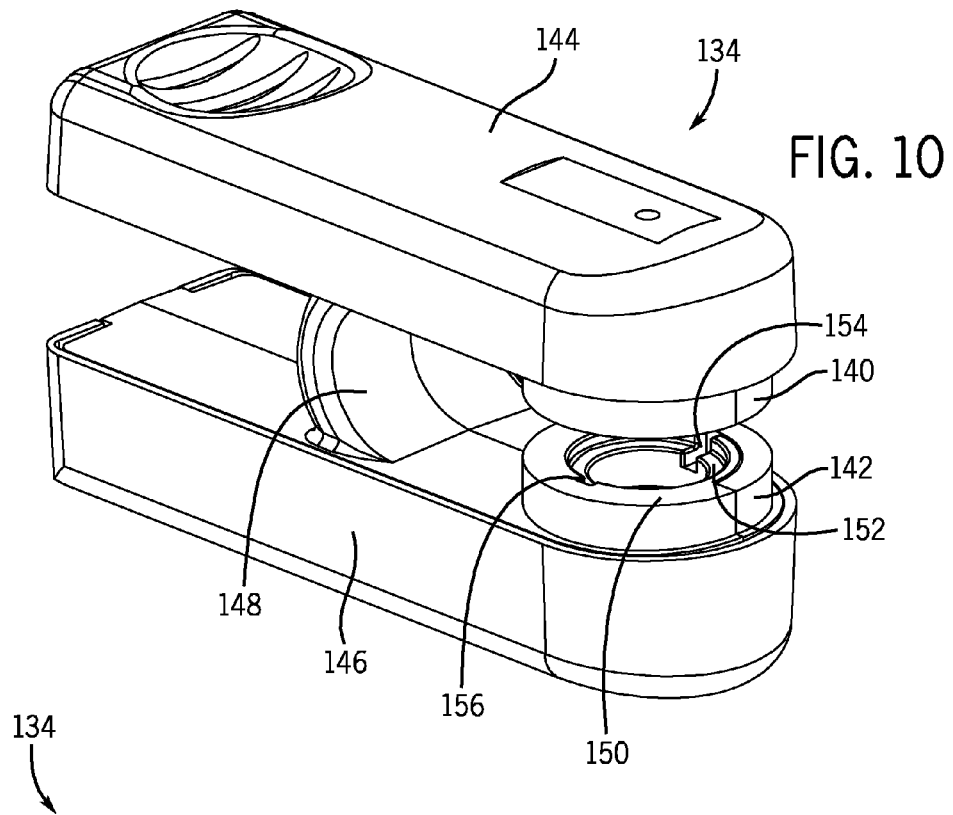

FIG. 10 is a perspective view showing a sensor clip assembly constructed in accordance with an embodiment of the invention.

Figure 11:
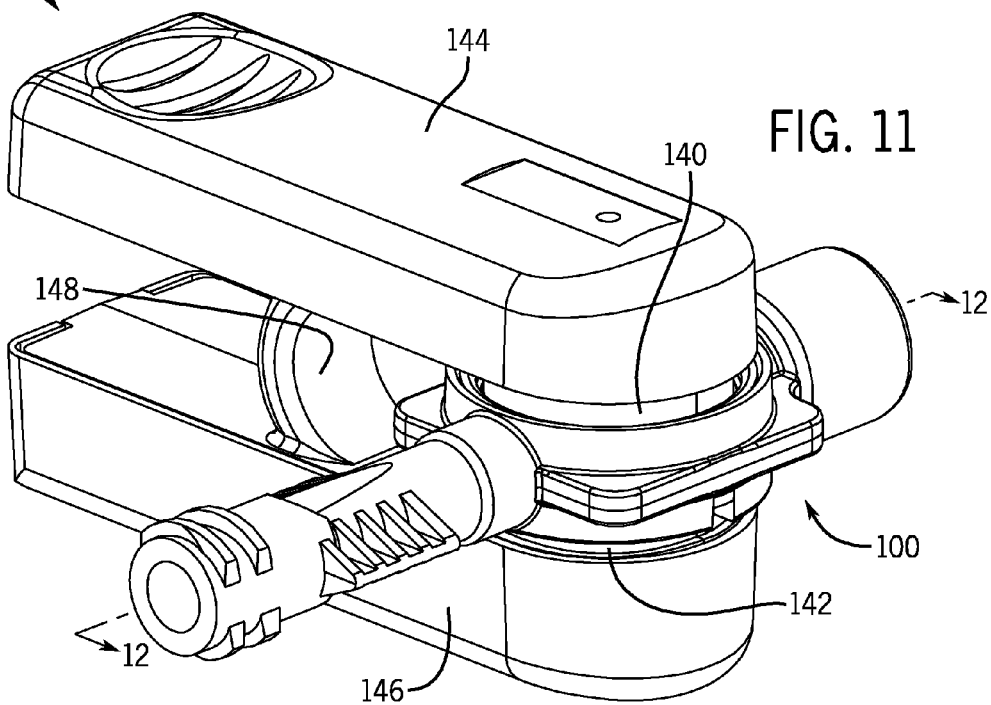

FIG. 11 is a perspective view showing the sensor clip assembly of FIG. 10 engaged with the blood chamber of FIG. 6.

Figure 12:
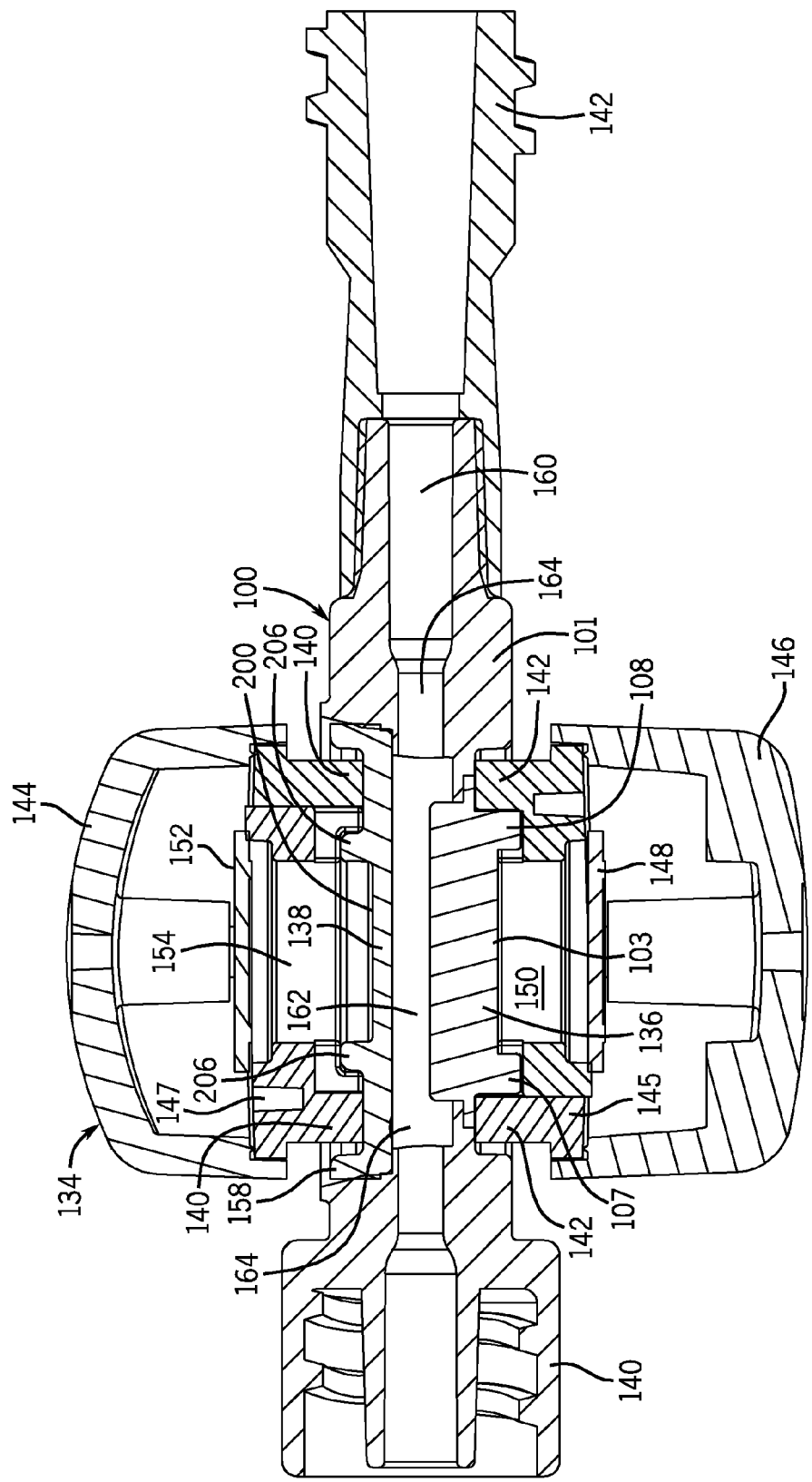

FIG. 12 is a longitudinal sectional view of taken along line 12-12 in FIG. 11.

DETAILED DESCRIPTION

Prior Art

Figure 1:
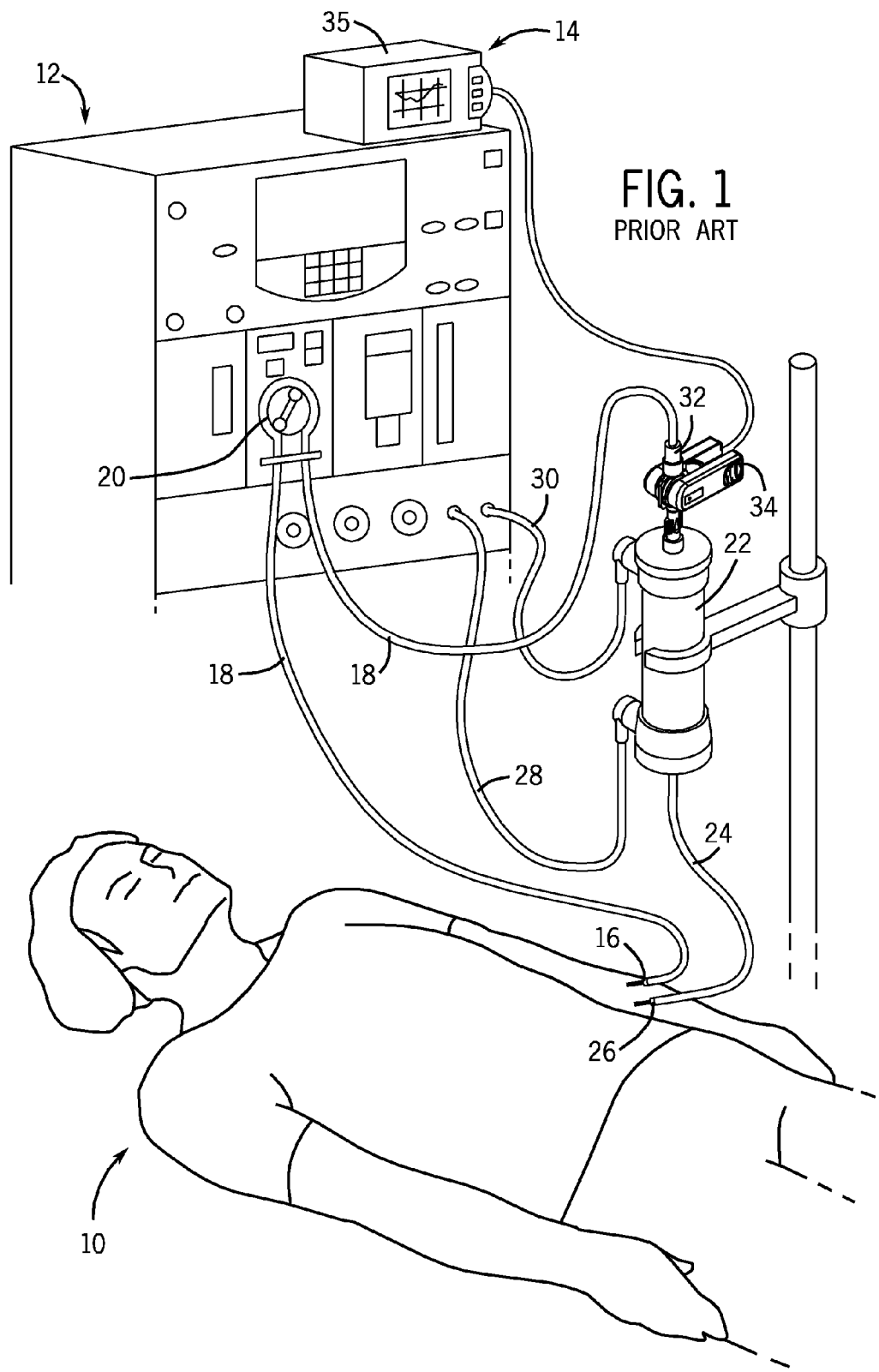
FIG. 1 is a perspective view of a patient undergoing hemodialysis treatment with a non-invasive, optical blood monitor monitoring the patient's blood in real-time as it passes through extracorporeal tubing in the hemodialysis system utilizing a prior art blood chamber and sensor clip assembly.

FIG. 1 illustrates a patient 10 undergoing hemodialysis treatment with a conventional hemodialysis system 12, and also illustrates a non-invasive, optical blood monitor 14. A typical hemodialysis clinic will have several hemodialysis systems 12 for treating patients.

An input needle or catheter 16 is inserted into an access site of the patient 10, such as shunt in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer 22 to the patient through extracorporeal tubing 24 and a return needle or catheter 26. The extracorporeal blood flow in the United States generally receives a heparin drip to prevent clotting although that is not shown in FIG. 1. Excess fluids and toxins are removed by clean dialysate liquid which is supplied to the dialyzer 22 via tube 28 and removed for disposal via tube 30. A typical hemodialysis treatment session in the United States takes about 3 to 5 hours. In a typical hemodialysis treatment as described in FIG. 1, the access site draws arterial blood from the patient. If no arterial access is available then a venous catheter may be used to access the patient's blood. As mentioned, other dialysis applications such as low flow Continuous Renal Replacement Therapy (CRRT) sometimes used in the Intensive Care Unit and perfusion measurements during cardiac surgery can measure venous blood from the patient. Current art indicates that oxygen saturation levels in venous blood correlate to the cardiac output for the patient. The typical blood monitor 14 shown in FIG. 1 can be used in these other applications as well.

The optical blood monitor 14 includes a blood chamber 32, a sensor clip assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photoemitters that emit light at substantially 810 nm (e.g. 829 nm), which is isobestic for red blood cells, substantially 1300 nm, which is isobestic for water, and at substantially 660 nm, which is sensitive for oxygenated hemoglobin. The blood chamber 32 includes lenses so that the sensor emitters and detector(s) can view the blood flowing through the blood chamber 32, and determine the patient's real-time hematocrit value and oxygen saturation value using ratiometric techniques generally known in the prior art.

Figure 2:
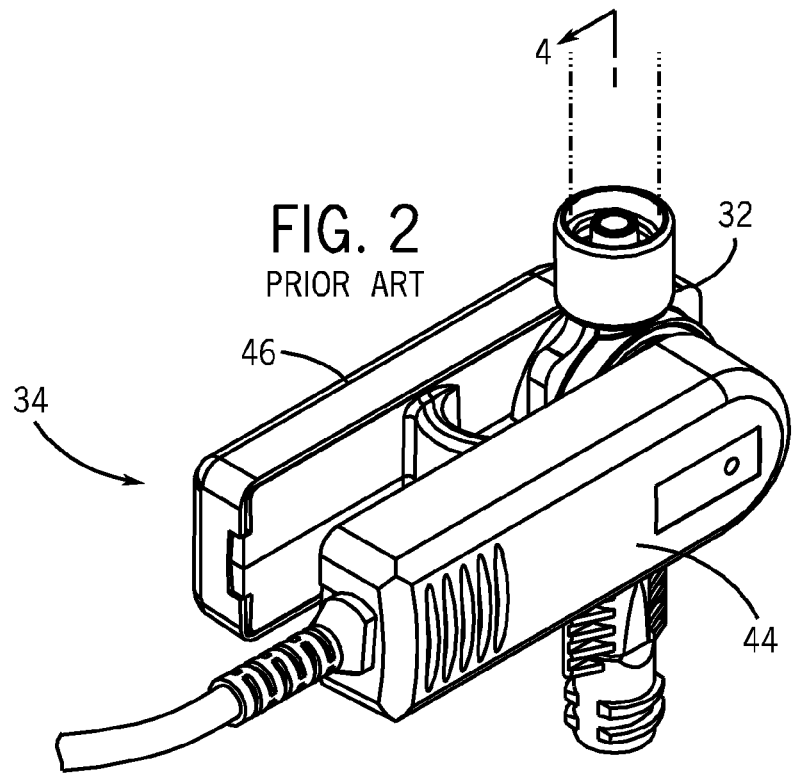
FIG. 2 is a perspective view showing a prior art sensor clip assembly for the optical blood monitor clipped on to a prior art blood chamber connected in the extracorporeal tubing of the hemodialysis system.
Figure 3A:
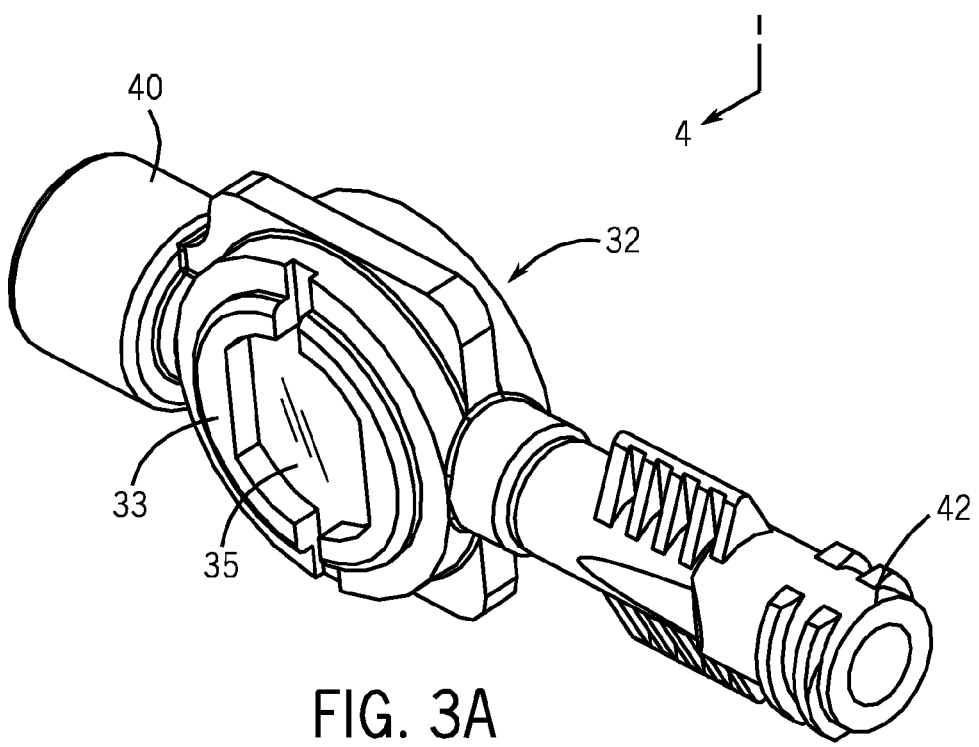
FIG. 3A is a detailed view of the prior art blood chamber shown in FIG. 2.
Figure 3B:
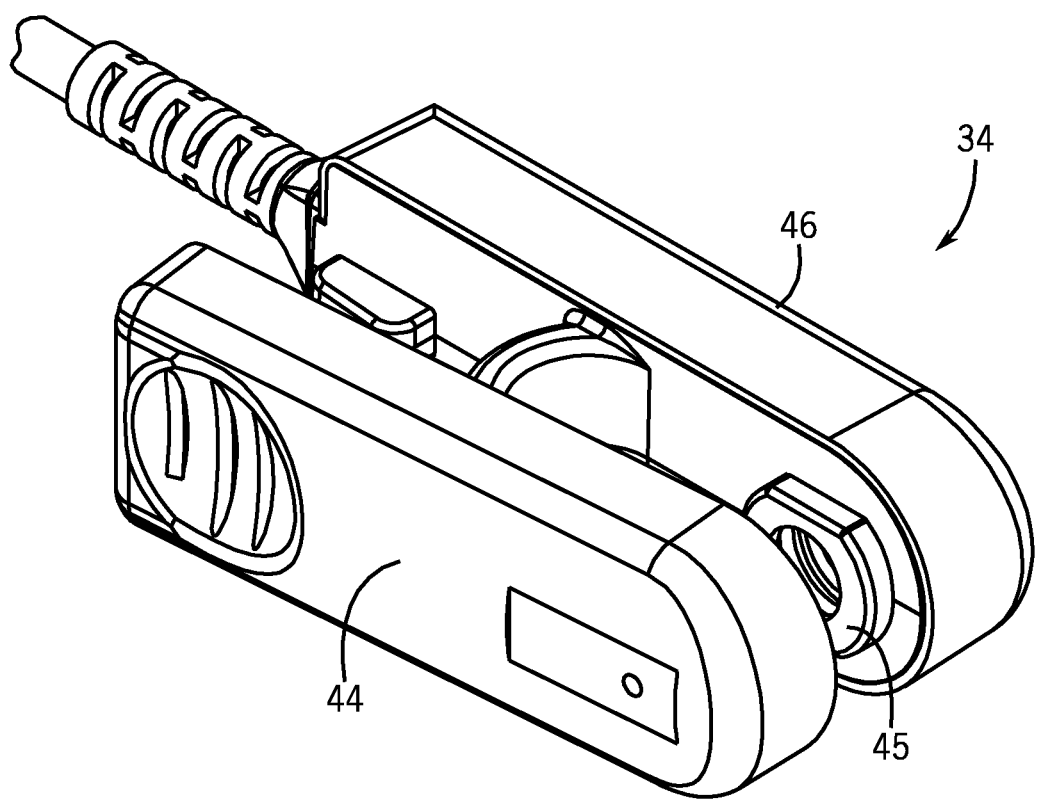
FIG. 3B is a detailed view of the prior art sensor clip assembly shown in FIG. 2.
Figure 4:
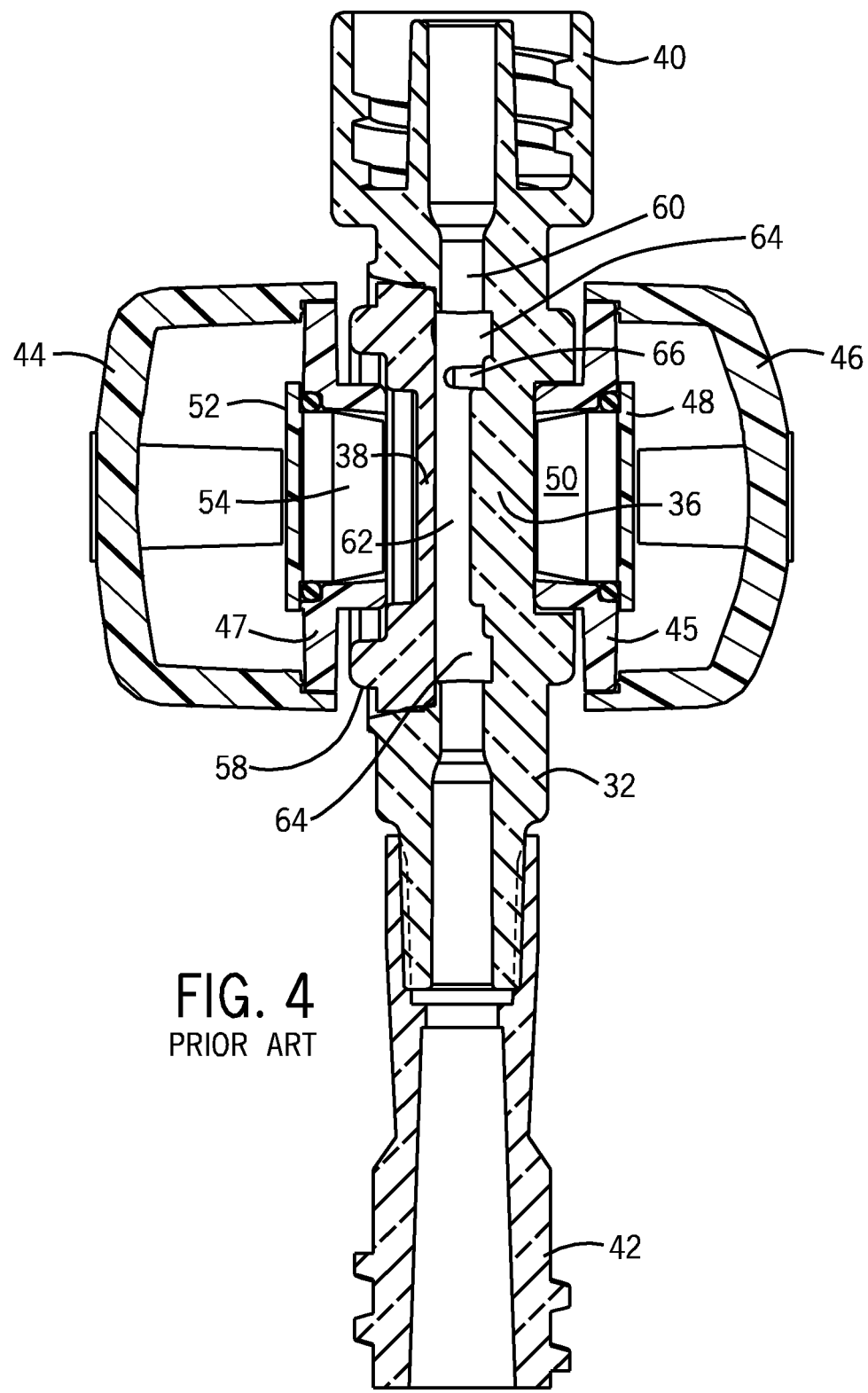
FIG. 4 is a cross-sectional view taken along line 4-4 of the prior art blood chamber shown in FIG. 2.

Referring to now FIGS. 2-4, the body of a prior art blood chamber 32 is made of molded, medical grade, clear polycarbonate. It includes a raised, stepped rim 33 having a double-D configuration surrounding the substantially flat viewing lens 35 (see FIG. 3A). It also includes two viewing windows 36, 38 (see FIG. 4). The inlet 40 and outlet 42 are designed to be compatible with standard medical industry connecting devices, conventionally known as luer lock connectors. In the blood chamber 32 shown in FIGS. 2-4, the inlet 40 is integrally molded with the blood chamber 32, whereas the outlet 42 consists of a suitable off-the-shelf connection adapter bonded to the body of the blood chamber 32 (alternatively, tubing can be attached directly to the body in place of connector 42). The sensor assembly 34 includes an emitter subassembly 44 and a detector subassembly 46. Referring to FIG. 3B, the emitter and detector heads (see, reference no. 45) both have a double-D configuration which corresponds to the double-D configuration of the blood chamber 32. The interlocking double-D configuration serves to fix the sensor clip 34 in a predetermined orientation when it is clipped into place over the blood chamber 32. Fixing the sensor clip 34 in a predetermined position is important for measurement accuracy because the system is calibrated for that predetermined position.

The housings 44 and 46 for the sensor clip assembly 34 include an inner housing frame 45, 47 which connects to the outer housing shells 44, 46. Each side of the inner housing frame 45, 47 provides an opening into which the molded diffusion lenses 50, 54 are mounted. The sensor assembly 34 is a spring-loaded clip assembly adapted to be removably mounted to the blood chamber 32, as shown in FIG. 2. Both sides of the blood chamber 32 are molded such that the clip 34 will reside in a predetermined position when mounted to the blood chamber 32. As mentioned, blood chamber 32 is a single-use clear polycarbonate component. Between patient treatments, the blood chamber 32 is replaced along with the extracorporeal tubing 18, 24, and blood filter 22.

As best shown in FIG. 4, an emitter circuit board 48 containing LEDs emitting light at substantially 660 nm, 810 nm and 1300 nm is mounted within the housing for the sensor subassembly 46. The photoemitters on the LED circuit board 48 emits visible and infrared light through a molded lens 50 that is mounted in the clip loop housing 45, and direct visible and infrared light through the viewing window 36 for the blood chamber 32. The controller 35 (FIG. 1), controls the operation of the respective LED emitters and detector(s) in order to multiplex the independent wavelength measurements so that the emitter and respective detector measurements remain correlated. Another circuit board 52 contains photo detectors, at least one made of silicon to detect light intensity at substantially 810 nm and 660 nm, and at least one made of InGaAs to detect light intensity at 1300 nm. The detector circuit board 52 is mounted within the housing for the detector subassembly 44. A molded lens 54 is mounted in the clip loop housing 47 on the detector side of the clip covered by housing 44. The controller 35 includes data acquisition hardware and software which receives signals proportional to the intensities detected by the InGaAs and Si detector diodes. The viewing window 38 in the blood chamber 32 facilitates transmission of visible and infrared light at the respective wavelengths to the detectors on the circuit board 52 of the detector subassembly 44. Note that the viewing window 38 is molded into a separate insert 58 (referred to as the lens body 58) that is sonically welded to the body of the blood chamber 32. Blood flows from the inlet 40 through the passageway 60 to a central viewing region 62, also referred to herein as an internal blood flow cavity 62. The internal blood flow cavity provides a substantially flat, thin (e.g. less than 0.1 inches) viewing region for the blood flowing through the blood chamber 36. The multiplexed visible or infrared light at the three selected wavelengths, namely about 810 nm, 1300 nm and 660 nm, are transmitted through the blood flowing through the flat viewing region provided by internal blood flow cavity 62, as well as through the viewing windows 36, 38 in the chamber 32. A moat 64 surrounds the flat viewing region 62. The moat 64 is somewhat deeper than the flat viewing region 62. The moat helps distribute non-laminar flow evenly and steadily through the viewing region and provides a thicker region of blood which under most normal operating conditions optically isolates the detectors from detecting ambient or ducted light that does not pass through the direct path through the blood in the blood flow chamber. One or more turbulence posts 66 are located immediately upstream of the viewing region 62 to create steady eddy currents in the flow across the viewing region 62.

Figure 5A:
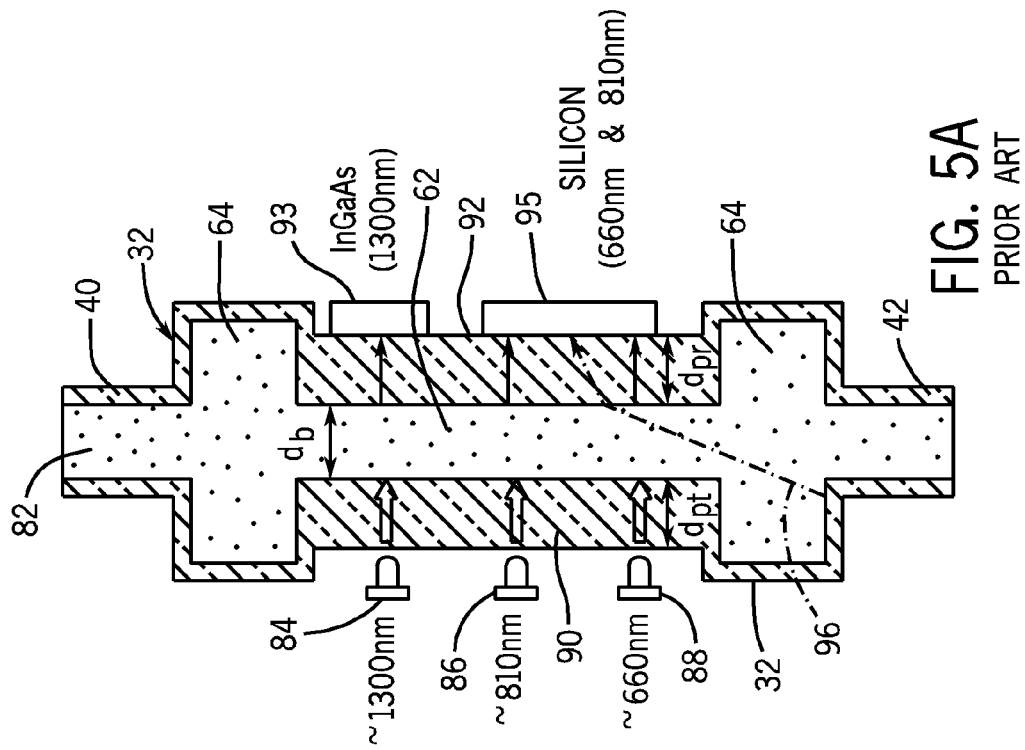
FIG. 5A is a schematic drawing similar to FIG. 5 further illustrating the effect of ambient or ducted light that does not pass through the direct path through the blood in the blood flow chamber.
Figure 5:
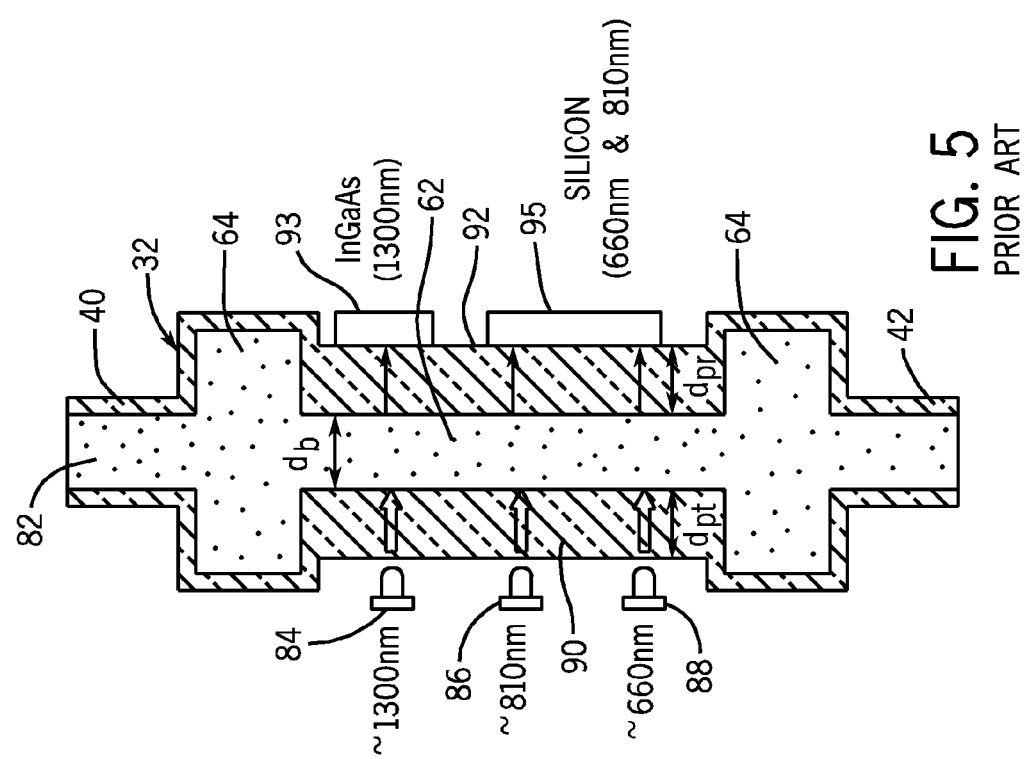
FIG. 5 is a schematic drawing illustrating the detection of light and infrared light at various wavelengths through the blood chamber in order to monitor the hematocrit and oxygen saturation of the blood passing through the blood chamber.

FIG. 5 is a schematic illustration of a prior art blood chamber 32 with a patient's blood 82 flowing through the chamber 32. As described above, the blood 82 enters the blood chamber through an inlet 40 and then flows into a moat 64 surrounding the flat viewing area 62. The distance across the viewing area 62 is given by the arrow labeled $d_b$, which signifies the thickness of the blood flowing through the flat viewing area 62. After the blood leaves the flat viewing area 62, it flows into the moat 64 located on the other side of the viewing area 62 and out of the chamber through the outlet 42. FIG. 5 shows three LED emitters 84, 86 and 88. LED 84 emits infrared light at substantially 1300 nm, LED 86 emits infrared light at substantially 810 nm, and LED 88 emits red light at substantially 660 nm. As mentioned, each of the LEDs 84, 86, 88 emits light at a fixed average intensity. The LEDs are pulsed on for a time period such that it is on at a time when the other LEDs are not on (i.e., timed-based multiplexing), although other methods of multiplexing are possible. As shown in FIG. 5, light from each LED emitter 84, 86, 88 is first transmitted through the clear polycarbonate transmission window 90 in the blood chamber 32, then through the blood flowing through the flat viewing region 62, and finally transmitted through the clear polycarbonate receiving window 92 on the other side of the blood chamber 32. An indium gallium arsenide detector 93 detects the intensity of the 1300 nm light wave that is transmitted through the walls of the blood chamber 32 and the blood flowing through the flat viewing region 92. A silicon detector 95 detects the intensity of the light at 810 nm and at 660 nm transmitted through the walls of the blood chamber 32 and the blood flowing through the flat viewing region 62.

The intensity of the light at each of the various wavelengths is reduced by attenuation and scattering from the fixed intensity of the light emitted from each of the LEDs 84, 86, 88. Beers Law, for each wavelength of light, describes attenuation and scattering as follows:

$$i_n = I_{o\text{-}n} e^{-\epsilon_p X_p d_{pt}} e^{-\epsilon_b X_b d_b} e^{-\epsilon_p X_p d_{pr}} \qquad \text{Eq. (3)}$$

where $i_n$=received light intensity at wavelength n after attenuation and scattering; $I_{o\text{-}n}$=transmitted light intensity at wavelength n incident to the measured medium; e=the natural log exponential term; $\epsilon$=the extinction coefficient for the measured medium (p—polycarbonate, b—blood); X=the molar concentration of the measured medium (p—polycarbonate, b—blood); and d=the distance through the measured medium (pt—transmitting polycarbonate, b—blood, pr—receiving polycarbonate).

Since the properties of the polycarbonate blood chamber do not change, the first and third exponential terms in the above Equation (3) are normally assumed in the prior art to be constants for each wavelength. Mathematically, these constant terms are multiplicative with the initial constant term $I_{o\text{-}n}$ which represents the fixed intensity of the radiation transmitted from the respective LED emitter 84, 86, 88. For simplification purposes, Equation (3) if often rewritten in the following form using bulk extinction coefficients and a modified initial constant $I'_{o\text{-}n}$ as follows:

$$i_n = I'_{o\text{-}n} * e^{-\alpha_b d_b} \quad \text{Eq. (4)}$$

where $i_n$=received light intensity at wavelength "n" after attenuation and scattering as though the detector were at the receive blood boundary; $\alpha$=the bulk extinction coefficient for blood; $\alpha_b = \epsilon_b X_b$; and $I'_{o\text{-}n}$ equals the equivalent transmitted radiation intensity at wavelength n boundary accounting for losses through the blood chamber walls.

Using the approach defined in Equation (4) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values $\alpha$ for the red blood cells and the water constituents in the blood chamber, respectively. Therefore, the following mathematical function defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \quad \text{Eq. (5)}$$

where $i_{810}$ is the detected infrared intensity of the photoreceiver 95 (FIG. 5) at 810 nm, $i_{1300}$ is the detected infrared intensity of the photodetector 93 (FIG. 5) at 1300 nm and $I_{0-810}$ and $I_{0-1300}$ are constants representing the infrared light intensity incident on the blood accounting for losses through the blood chamber at 810 nm and 1300 nm respectively. The above equation holds true assuming that the flow of blood through the blood chamber 32 is in steady state, i.e. steady pressure and steady flow rate. The preferred function f[ ] is a second order polynomial having the following form:

$$HCT = f = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C. \quad \text{Eq. (6)}$$

A second order polynomial is normally adequate as long as the infrared radiation incident at the first and second wavelengths is substantially isobestic.

The oxygen saturation level, or the oxygenated hemoglobin level, is determined using a ratiometric equation for the intensity of red light at 660 nm detected by detector 95, FIG. 5 and the intensity of infrared light at 810 nm detected by detector 95, FIG. 5. The form of the ratiometric model for determining oxygen saturation level is as follows:

$$SAT = g\left[\frac{\ln\left(\frac{i_{660}}{I_{0-660}}\right)}{\ln\left(\frac{i_{810}}{I_{0-810}}\right)}\right] \quad \text{Eq. (7)}$$

where $i_{660}$ is the detected intensity of the photoreceiver at 660 nm, $i_{810}$ is the detected intensity of the photodetector at 810 nm and $I_{0-660}$ and $I_{0-810}$ are constants representing the light intensity incident on the blood accounting for losses through the blood chamber. The function g[ ] is a mathematical function based on experimental data to yield the oxygen saturation level, again preferably a second order polynomial $$SAT = g = A\left[\frac{\ln\left(\frac{i_{660}}{I_{0-660}}\right)}{\ln\left(\frac{i_{810}}{I_{0-810}}\right)}\right]^2 + B\left[\frac{\ln\left(\frac{i_{660}}{I_{0-660}}\right)}{\ln\left(\frac{i_{810}}{I_{0-810}}\right)}\right] + C. \quad \text{Eq. (8)}$$

FIG. 5A is a schematic drawing similar to FIG. 5 further illustrating the effect of ambient ducted light that does not pass through a direct path through the blood in the blood flow chamber. In this regard, ray 96 is illustrative of ambient or ducted light. If ambient or ducted light is sensed by the detectors 93, 95, measurement inaccuracies can occur if not appropriately accounted for by signal processing. In accordance with the invention, it has been found desirable to physically eliminate the effect of ambient light that might otherwise be detected by the photo detectors 93, 95. As mentioned, this is done in accordance with the invention by providing shrouds on the sensor clip assembly and providing a single-use blood chamber with a mating configuration. It may also be desirable to construct the chamber body of an opaque material to further attenuate ambient light.

Present Invention

FIGS. 6 through 9 illustrate a blood chamber 100 constructed in accordance with a preferred embodiment of the present invention.

FIG. 7 illustrates a first exterior side of the blood chamber 100. The blood chamber 100 is constructed from a molded chamber body 101 which includes an inlet and an outlet as well as a first viewing lens 103. In accordance with the invention, the chamber body 101 may be molded entirely of clear, medical grade polycarbonate material or other suitable material. Alternatively, it may be desirable to use a lens insert 102 made of entirely clear, medical grade polycarbonate, and over mold the remaining parts of the chamber body 101 with an opaque material such as a blue-tinted medical grade polycarbonate. In either case, the preferred chamber body 101 includes a circular viewing lens 103 and a separate, distinct shroud mating surface 104 located circumferentially around the viewing lens 103. The shroud mating surface 104 is sunken with respect to the surface of the viewing lens 103, and is adapted to receive a shroud on a sensor clip assembly as will be discussed in more detail below. FIG. 7 also illustrates two anti-rotation tabs 107, 108 formed on the exterior surface of the blood chamber 100. The anti-rotation tabs 107, 108 are raised above the surface of the lens 103.

FIG. 6 illustrates the other exterior side of the blood chamber 100. This side of the blood chamber 100 includes a second circular viewing lens 200. The region between the second viewing lens 200 in FIG. 6 and the first viewing lens 103 in FIG. 7 consists of lens material (e.g. clear, medical grade polycarbonate) and the blood flowing through the internal blood flow cavity within the blood chamber 100. The lenses 103, 200 thus provide a viewing window for the sensor clip assembly to monitor the blood flowing through the blood chamber 100. Referring still to FIG. 6, an upstanding annular wall 206 surrounds the second viewing lens 200. An annular well 204 is formed between the upstanding, annular wall 206 and a peripheral wall 210 on the blood chamber 100. The floor of this annular well 204 is another shroud mating surface which again is separate and distinct from the viewing lens 200. In accordance with the preferred embodiment of the invention, a lens body 202 containing the viewing lens 200, the upstanding wall 206, and the surrounding annular well 204, is molded of a clear polycarbonate material and is attached via sonic welding or other means to the chamber body 101 during the manufacturing process.

FIG. 9 shows the cross section of the blood chamber 100. The chamber body 101 including a substantially flat internal wall 110 that forms part of the internal blood flow cavity 120. The lens body 202 attached to the chamber body 101 also includes a substantially flat internal wall 112 that is substantially parallel to the substantially flat internal wall 110 on the chamber body 101. The flat internal wall 112 on the lens body 202 is separated from the flat internal wall 100 on the chamber body 101 by a predetermined fixed distance. The first viewing lens 103 on the chamber body 101 and the second viewing lens 200 on the lens body 202 serve as viewing windows 136 and 138 (FIG. 12) for blood flowing through the internal blood flow cavity 120. The chamber body 101 (FIG. 9) includes a first port 122 and a channel 124 (inlet) that are in fluid communication through a first opening 126 in the internal blood flow cavity 120. The chamber body 101 also includes a second port 128 and channel 130 (outlet) that are in fluid communication through a second opening 132 in the internal blood flow cavity 120.

FIG. 10 illustrates a sensor clip assembly 134 configured in accordance with a preferred embodiment of the invention. The sensor clip assembly 134 is used to monitor the patient's blood flowing through the blood chamber 100. As depicted in the embodiment illustrated in FIG. 11, the LED emitter arm 144 and the photodetector arm 146 are affixed into place around a blood chamber 100 in order to monitor the hematocrit, hemoglobin, change in blood volume and oxygen saturation level, and/or other blood constituents of blood flowing through the blood chamber 100. Accordingly, the sensor clip assembly 134 preferably includes a spring biased bridge 148 or equivalent structure to attach a sensor clip assembly 134 to a blood chamber 100.

The sensor clip assembly 134 includes an LED emitter arm 144 and a photodetector arm 146, which are connected via a spring biased bridge 148. The LED emitter arm 144 contains an emitter subassembly with at least two LED emitters, one emitting infrared light or radiation at a first wavelength ($\lambda_1$) of about 1300 nm and another emitting infrared light or radiation at a second wavelength ($\lambda_2$) of about 810 nm (e.g. 829 nm). The LED emitter preferably also includes a third LED emitter for emitting infrared light or radiation at a third wavelength ($\lambda_3$) of about 660 nm. Other wavelengths could be substituted or added to measure additional blood constituents or properties of other fluids. The detector arm 146 contains preferably two types of photodetectors: a silicon photo detector to detect the approximate 660 and 810 nm wavelengths, and an indium gallium arsenide photo detector to detect the approximate 1300 nm wavelength. As configured in the embodiment depicted in FIGS. 10-12, the sensor clip assembly 134 emits infrared light or radiation through the viewing lenses 103 and 200 and through the viewing windows 136 and 138 and through the blood flowing through the internal blood flow cavity 120 of the blood chamber 100.

The sensor clip assembly 134 preferably includes a shroud 140 on the inner housing piece of the emitter arm 144 subassembly to prevent ambient light from entering the blood chamber through the viewing lenses or the lens bodies and a shroud 142 on the inner housing piece of the detector arm 146 subassembly to prevent ambient light from entering the blood chamber through the viewing lenses or the lens bodies.

Referring now to FIGS. 10-12, the shrouds 140 and 142 are preferably mirror images of one another. The description of shroud 140 on the emitter arm 144 therefore is representative and applies equally to the description of the shroud 142 on the detector arm 146. Referring in particular to FIG. 10, it can be seen the shroud 142 contains an outer annular ledge or step surface 150 and an inner annular ledge or step surface 152. The difference in the heights of the step surfaces 150, 152 corresponds to the height of the annular wall 206 on the second exterior side of the blood chamber 100 (see, FIG. 6), and also to the height at which the lens surface 103 is raised above the sunken well 104 on the first side of the blood chamber 100 (see, FIG. 7). Preferably, the shape and surface area of the outer annular step surface 150 is substantially equal to the shape and surface area of the respective shroud mating surfaces 104, 204 on the blood chamber 100, see FIGS. 11 and 12, in order to maximize the blocking of ambient light.

Still referring to FIG. 10, the shroud 142 illustrated in FIG. 10 includes slots 154, 156 that are adapted to receive the anti-rotation tabs 107, 108 on the blood chamber 100 (see FIG. 7). The shroud 140 on the emitter arm 144 includes identical slots so that the sensor clip assembly 134 may be clipped on to the blood chamber 100 in either direction. In either direction, however, the sensor clip assembly will be fixed in a predetermined position and rotational orientation corresponding to the factory calibration for the optical monitoring system. As mentioned previously, the shape of the anti-rotation tabs 107, 108 and the corresponding slots 154, 156 may take on any reasonable shape, and furthermore as previously mentioned aspects of the invention may be implemented using alternative anti-rotation configurations.

FIG. 12 shows a cross-sectional view of sensor clip assembly 134 clipped on to the blood chamber 100. Referring specifically to the blood chamber 100 as shown in FIG. 12, the blood chamber 100 includes two viewing windows 136 and 138. Surface 103 of the first viewing lens 136 is exposed on the first exterior side of the blood chamber 100 (see FIG. 7). The exterior surface 206 of the other viewing window 138 is exposed on the first side of the blood chamber 100 (see FIG. 6). The blood chamber 100 includes an inlet 140 and outlet 142 that are designed to be compatible with standard medical industry connecting devices conventionally known as lure lock connectors. In the blood chamber 100 shown in FIG. 12, the inlet 140 is integrally molded with the blood chamber 100, whereas the outlet 142 consists of a suitable off-the-shelf connector adapter bonded to the body of the blood chamber 100. Alternatively, tubing can be attached directly to the body of the blood chamber 100 in place of the connector 142.

The LED emitter subassembly 144 as shown in FIG. 12 contains an emitter circuit board 152 containing LEDs emitting light at substantially 660 nm, 810 nm and 1300 nm. The LEDs radiate light through the molded diffusing lens 154. As shown in FIG. 12, the shroud 140 on the emitter sub-housing 144 is spaced apart from the molded diffusing lens 154. In addition, the shroud 140 extends towards the detector subassembly 146 beyond the location of the diffusing lens 154.

The photodetector subassembly 146 includes a circuit board 148 to which the silicon photodetector can detect intensity at 810 nm and 660 nm, and the indium gallium arsenide photodetector to detect light intensity at 1300 nm are mounted. Again, the photodetectors are mounted to receive light energy through a molded diffusing lens 150. FIG. 12 shows that the shroud 142 is spaced apart from the diffusing lens 150 and also that the shroud 142 extends beyond the diffusing lens 150 toward the emitter subassembly 144. In FIG. 12, the anti-rotation tabs 107, 108 are shown in cross-section as taken along the line 12-12 in FIG. 11.

The viewing window 136 as shown in the embodiment in FIG. 12 is either part of a separate lens insert which is then over molded to the remainder of the chamber body 101 if an opaque body is desired or this lens can be molded as part of the chamber body 101 as one piece. The viewing window 138 on the other side of the blood chamber 100 is part of a separately molded lens body, which is sonically welded or otherwise adhered to the chamber body.

Further referring to FIG. 12, blood flows from the inlet into the central viewing region which has been referred to previously as the internal blood flow cavity 162. The internal blood flow cavity provides a substantially flat, thin (e.g. less than 0.1 inches) viewing area for the blood flowing through the blood chamber 100. The multiplexed visible or infrared light at the selected wavelengths are transmitted through the blood flowing through the flat viewing region as well as through the viewing windows 136 and 138. A moat 164 surrounds the flat viewing region 162. The moat 164 is somewhat deeper than the flat viewing region 162, and servers in part to distribute non-laminate flow evenly and steadily through the viewing region. Though optional, when used the moat 164 also provides a thicker region of blood which under most normal operating conditions optically isolates the detectors from ducted or ambient light that does not pass through the direct path from the emitters through the blood to the detectors.

The viewing lenses 103, 200 are preferably made of clear, medical grade polycarbonate material which is molded with a polished finish in order to facilitate reliable light transmission, e.g. Bayer Makrolon FCR 2458-5515 (no re-grind allowed), which is blood contact approved, USPXX11 class VI. It is expected that the material be certified as to grade number, lot number and date of manufacture. Moreover, the viewing lenses should contain splay, bubbles or marks when looking through the display window viewed from twelve inches with the normal eye. The molded parts should be produced with no lose foreign material greater than 0.1 mm$^2$ and no embedded foreign material greater than 0.2 mm$^2$ and no mold release should be use, and any lubrications should be food grade and not silicon based. The mold finish is preferably SPIA3 (scale) except along the surfaces for the viewing windows which the finish should preferably be at least SPIA1. Parts should be cleaned and free and dirt, oils and other foreign matter before use.

While the lens portions 103 and 200 should be made of clear material, it may be desirable to tint the remaining portions of the chamber body. For example, it may be desirable to use a blue-tinted polycarbonate material for the remaining portions of the chamber body.

The described use and embodiment of the invention is to be considered in all respects as only illustrative and not restrictive.

What is claimed is:

1. A blood chamber for use in an optical blood monitoring system having a sensor clip assembly with first shroud surrounding photoemitters on one side of the sensor clip assembly and a second shroud surrounding photodetectors on the other side of the sensor clip assembly, the blood chamber comprising:

an inlet, an outlet and an internal blood flow cavity;

a first exterior side having a first viewing area and a separate, distinct shroud mating surface located outside of the first viewing area, the shroud mating surface on the first exterior side being adapted to engage a shroud on a sensor clip assembly when the sensor clip assembly is clipped on to the blood chamber;

a second exterior side having a second viewing area and a separate, distinct shroud mating surface located outside of the second viewing area, the shroud mating surface on the second exterior side being adapted to engage a shroud on a sensor clip assembly when the sensor clip assembly is clipped over the blood chamber;

an upstanding wall on the second exterior side outside of the second viewing area and separating the second viewing area from the shroud mating surface on the second exterior side of the blood chamber such that a well is formed around the second viewing area, a floor of the well being the shroud mating surface on the second exterior side of the blood chamber;

wherein each of the first and second viewing areas has a substantially flat exterior surface that is parallel to and aligned with the other viewing area.

2. The blood chamber as recited in claim 1 further comprising:

a molded chamber body that includes the inlet and the outlet;

a first molded lens body that includes the first exterior side with the first viewing area; and a second molded lens body that includes the second exterior side with the second viewing area;

wherein the first and second molded lens bodies are attached to the molded chamber body during the manufacturing of the blood chamber.

3. The blood chamber as recited in claim 1 wherein at least one anti-rotation tab is formed on the first exterior side, said anti-rotation tab being adapted to inter-engage with a slot on a shroud of a sensor clip assembly.

4. The blood chamber as recited in claim 3 wherein the anti-rotation tab is raised above the viewing area on the first side of the blood chamber.

5. The blood chamber as recited in claim 1 wherein the exterior surface of the first viewing area is raised above the shroud mating surface such that a well is formed around the raised viewing area, the floor of the well being the shroud mating surface on the first exterior side of the blood chamber.

6. The blood chamber as recited in claim 1 wherein the exterior surface of the second viewing area and the shroud mating surface on the second exterior side of the blood chamber are located at substantially the same depth relative to the upstanding wall.

7. The blood chamber as recited in claim 1 wherein:

the exterior surface of the first viewing area is raised above the shroud mating surface on the first exterior side of the blood chamber such that a well is formed around the raised viewing area; and the height of the raised viewing area on the first exterior side of the blood chamber above the well on the first exterior side of the blood chamber is substantially equal to the height of the wall on the second exterior side of the blood chamber.

8. The blood chamber as recited in claim 1 wherein the viewing areas are circular.

9. The blood chamber as recited in claim 8, wherein the shroud mating surfaces are annular.

10. The blood chamber as recited in claim 1 further comprising:
a molded chamber body that includes the inlet, outlet and the first exterior side with the first viewing area; and
a molded lens body that includes the second exterior side with the second viewing area;
wherein the molded lens body is attached to the molded chamber body as part of manufacturing the blood chamber.

11. The blood chamber as recited in claim 10, wherein the first viewing area of the chamber body comprises a clear polycarbonate material and the remainder of the molded chamber body comprises an opaque polycarbonate material.

12. The blood chamber as recited in claim 11, wherein the molded lens body is made entirely from clear polycarbonate material and is attached to the chamber body during the manufacturing process.

13. An optical blood monitoring system comprising:
extracorporeal tubing for passing blood drawn from a patient;
a blood chamber for receiving blood flowing through the extracorporeal tubing, the blood chamber defining a flow path through an internal blood flow cavity and providing a viewing area for optical monitoring of the blood, the blood chamber including:
an inlet, an outlet and an internal blood flow cavity;
a first exterior side having a viewing area and a separate, distinct shroud mating surface located outside of the viewing area, the distinct shroud mating surface being adapted to engage a shroud of a sensor clip assembly when the sensor clip assembly is clipped onto the blood chamber;
a second exterior side having a viewing area and a separate, distinct shroud mating surface located outside of the viewing area, the distinct shroud mating surface being adapted to engage a shroud of a sensor clip assembly when the sensor clip assembly is clipped onto the blood chamber;
wherein each viewing area has a substantially flat exterior surface that is parallel to and aligned with the other viewing area; and
a sensor clip assembly that monitors the patient's blood flowing through the blood chamber, the sensor assembly comprising:
an emitter subassembly with a first photoemitter for emitting light at a first wavelength ($\lambda 1$) through the viewing areas and blood flowing through the internal blood flow cavity of the blood chamber and a second photoemitter for emitting light at a second wavelength ($\lambda 2$) through the viewing areas and blood flowing through the internal blood flow cavity of the blood chamber;
a detector subassembly with at least one photodetector for detecting the intensity of the light at each of the first ($\lambda 1$) and second ($\lambda 2$) wavelengths after the light passes through the viewing areas and blood flowing through the internal blood flow cavity of the blood chamber;
an emitter shroud on the emitter subassembly surrounding the photoemitters and extending away from the emitter subassembly to a distance beyond a diffusing lens associated with the photoemitters and towards the detector subassembly to prevent at least ambient light from entering the blood chamber through a viewing area when the sensor clip assembly is clipped onto the blood chamber; and
a detector shroud on the detector subassembly surrounding the photodetectors and extending away from the detector subassembly to a distance beyond a diffusing lens associated with the at least one photodetector and toward the emitter subassembly to prevent at least ambient light from entering the blood chamber through a viewing area when the sensor clip assembly is clipped onto the blood chamber.

14. The system as recited in claim 13 further including a controller having a ratiometric model to calculate a hematocrit value (HCT) of the blood drawn from the patient and passing through the extracorporeal tubing and blood chamber, said ratiometric model to calculate the hematocrit value (HCT) being of the following form:

$$HCT = f\left[\frac{\ln\left(\frac{i_{\lambda 2}}{I_{0-\lambda 2}}\right)}{\ln\left(\frac{i_{\lambda 1}}{I_{0-\lambda 1}}\right)}\right]$$

where HCT is the hematocrit value determined by the ratiometric model;
$i\lambda 1$ is the detected light intensity at the first wavelength;
$i\lambda 2$ is the detected light intensity at the second wavelength;
Io–$\lambda 1$ is a calibration constant representing the light intensity of the first wavelength incident on the blood chamber taking into account the losses due to the blood chamber;
Io–$\lambda 2$ is a calibration constant representing the light intensity of the second wavelength incident on the blood chamber taking into account the losses due to the blood chamber; and
f is a function that fits log ratio mathematics to yield HCT.

15. The system as recited in claim 14 wherein the emitter subassembly contains a third photoemitter for emitting infrared light at a third wavelength ($\lambda 3$) through the viewing areas and blood flowing through the internal blood flow cavity of the blood chamber and wherein the photodetector is capable of detecting the intensity of the light at the third wavelength ($\lambda 3$) after the light passes through the viewing areas and blood flowing through the internal blood flow cavity of the blood chamber.

16. The system as recited in claim 15 wherein the controller contains a second ratiometric model to calculate oxygen saturation level (SAT), of the blood drawn from the patient in passing through the extracorporeal tubing and blood chamber, said second ratiometric model to calculate oxygen saturation level (SAT) being of the following form:

$$SAT = g\left[\frac{\ln\left(\frac{i_{\lambda 3}}{I_{0-\lambda 3}}\right)}{\ln\left(\frac{i_{\lambda 1}}{I_{0-\lambda 1}}\right)}\right]$$

where SAT is the oxygen saturation level determined by the ratiometric model;
$i\lambda 1$ is the detected light intensity at a first wavelength;
$i\lambda 3$ is the detected light intensity at a third wavelength;
Io–$\lambda 1$ is a constant representing the light intensity of the first wavelength incident on the blood chamber taking into account the losses due to the blood chamber;
Io–$\lambda 3$ is a constant representing the light intensity of a third wavelength incident on the blood chamber taking into account the losses due to the blood chamber; and
g is a function that fits log ratio mathematics to yield SAT.

17. The system as recited in claim 13 wherein each annular shroud is stepped with an inner annular step surface being positioned at a distance away from the respective subassembly that is less than distance that an outer annular step surface is positioned away from the respective subassembly.

18. The system as recited in claim 17 wherein the surface area of the outer annular step surface is substantially equal to the surface area of the shroud mating surface on the blood chamber.

19. The system as recited in claim 18 wherein the first exterior side of the blood chamber includes an anti-rotation tab.

20. The system as recited in claim 19 wherein at least one shroud contains a slot shaped to engage the anti-rotation tab.

21. The system as recited in claim 19 wherein both shrouds contain a slot shaped to engage the anti-rotation tab.

22. The system as recited in claim 13 wherein the viewing areas on the blood chamber are circular and the shrouds on the sensor clip are annular.

23. The system as recited in claim 22 wherein:
the exterior surface of the first viewing area on the blood chamber is raised above the shroud mating surface such that an annular well is formed around the raised viewing area;
the exterior surface of the second viewing area on the blood chamber is surrounded by an upstanding wall that separates the second viewing area from the shroud mating surface on the second exterior side of the blood chamber such that an annular well is formed around the second viewing area; and
each annular shroud on the sensor clip assembly is stepped and an inner annular step surface being positioned at a distance away from the respective subassembly that is less than a distance that an outer annular step surface is positioned away from the respective subassembly, said distance being substantially equal to the height of the wall on the second exterior side of the blood chamber and substantially equal to the height of the raised viewing area on the first exterior side of the blood chamber above the surrounding annular well.

24. The optical blood monitoring system as recited in claim 13 wherein at least one anti-rotation tab is formed on the first exterior side of the blood chamber, said at least one anti-rotation tab being adapted to inter-engage with at least one slot on the shroud of the sensor clip assembly.

25. The optical blood monitoring system as recited in claim 13 wherein an upstanding wall on the second exterior side of the blood chamber surrounds the second viewing area and separates the second viewing area from the shroud mating surface on the second exterior side of the blood chamber such that a well is formed around the second viewing area, the floor of the well being the shroud mating surface on the second exterior side of the blood chamber.

26. The optical blood monitoring system as recited in claim 13, wherein the blood chamber includes a molded chamber body comprising a polycarbonate material that is tinted blue and a molded lens body comprising a clear polycarbonate.

27. A method for monitoring at least one blood constituent, the method comprising:
connecting a blood chamber to extracorporeal tubing through which a patient's blood flows, said blood chamber having a body including an internal blood flow cavity between a first viewing area and a second viewing area;
attaching a sensor clip assembly having art emitter subassembly and a detector subassembly to the blood chamber so as to limit rotation of the sensor clip assembly relative to the blood chamber by engaging one or more anti-rotational tabs formed on the blood chamber with one or more slots formed in a shroud on the sensor clip assembly;
emitting light from the emitter subassembly at a first wavelength through the blood chamber and the patient's blood flowing through the blood chamber;
emitting light from the emitter subassembly at a second wavelength through the blood chamber and the patient's blood flowing through the blood chamber;
detecting the intensity of the light at the first wavelength with the detector subassembly after it has passed through the blood chamber and the patient's blood flowing therethrough;
detecting the intensity of the light at the second wavelength, with the detector subassembly after it passes through the blood chamber and the blood flowing therethrough;
calculating a concentration or value of a blood constituent from at least the detected light intensity at the first wavelength and the detected light intensity at the second wavelength; and
limiting ambient light from entering the first and second viewing areas and limiting light emitted from the emitter subassembly from ducting through the body of the blood chamber to the detector subassembly by surrounding the first viewing area with the shroud, where the shroud is a first shroud, and by surrounding the other of the first and second viewing areas with a second shroud.

28. The method for monitoring at least one blood constituent as recited in claim 27, wherein attaching the sensor clip assembly to the blood chamber so as to limit relative rotation of the sensor clip assembly and the blood chamber includes engaging one or more anti-rotational tabs formed on the blood chamber with one or more slots formed in a shroud on the sensor clip assembly.

29. A blood chamber for use in an optical blood monitoring system having a sensor clip assembly with first shroud surrounding photoemitters on one side of the sensor clip assembly and a second shroud surrounding photodetectors on the other side of the sensor clip assembly, the blood chamber comprising:
an inlet, an outlet and an internal blood flow cavity;
first and second exterior sides each having a viewing area and a separate and distinct shroud mating surface located outside of the viewing area, where the shroud mating surface on the first exterior side is adapted to engage a shroud on a sensor clip assembly when the sensor clip assembly is clipped on to the blood chamber;
one or more anti-rotation tabs formed on at least one of the first and second exterior sides, said one or more anti-rotation labs being adapted to inter-engage with one or more slots on the shroud of the sensor clip assembly;
wherein each of the viewing areas has a substantially flat exterior surface that is parallel to and aligned with the other viewing area.

30. The blood chamber as recited in claim 29 wherein the viewing areas are first and second viewing areas, the blood chamber further comprising:
a molded chamber body that includes the inlet and the outlet;
a first molded lens body that includes the first exterior side with the first viewing area; and
a second molded lens body that includes the second exterior side with the second viewing area;
wherein the first and second molded lens bodies are attached to the molded chamber body during the manufacturing of the blood chamber.

31. The blood chamber as recited in claim 30, wherein the first viewing area of the chamber body comprises a clear polycarbonate material and the remainder of the molded chamber body comprises a blue-tinted polycarbonate material.

32. A blood chamber as recited in claim 31, wherein each of the first and second molded lens body is made entirely from clear polycarbonate material and is attached to the chamber body during the manufacturing process.

33. The blood chamber as recited in claim 29 wherein the anti-rotation tab is raised above the viewing area.

34. The blood chamber as recited in claim 29 including an upstanding wall on the second exterior side outside of the viewing area and separating the viewing area from the shroud mating surface on the second exterior side of the blood chamber such that a well is formed around the viewing area, a floor of the well being the shroud mating surface on the second exterior side of the blood chamber.

35. The blood chamber as recited in claim 34 wherein the exterior surface of the viewing area and the shroud mating surface of the second exterior side of the blood chamber are located at substantially the same depth relative to the upstanding wall.

36. A blood chamber for use in an optical blood monitoring system having a sensor clip assembly with first shroud surrounding photoemitters on one side of the sensor clip assembly and a second shroud surrounding photodetectors on the other side of the sensor clip assembly, the blood chamber comprising:
   a chamber body that includes an inlet, an outlet and an internal blood flow cavity;
   first and second exterior sides of the chamber body each having a viewing area and a separate and distinct shroud mating surface located outside of the viewing area, where the shroud mating surface on the first exterior side is adapted to engage a shroud on a sensor clip assembly when the sensor clip assembly is clipped on to the blood chamber; and
   first and second lens bodies, which include the viewing areas, comprising a clear polycarbonate material and the remainder of the molded chamber body comprising a blue-tinted polycarbonate material;
   wherein each of the viewing areas has a substantially flat exterior surface that is parallel to and aligned with the other viewing area.

37. The blood chamber as recited in claim 36, wherein each of the first and second lens bodies is attached to the chamber body during a manufacturing process.

38. The blood chamber as recited in claim 36 including one or more anti-rotation tabs formed on at least one of the first and second exterior sides, said one or more anti-rotation tabs being adapted to inter-engage with one or more slots on the shroud of a sensor clip assembly.

39. The blood chamber as recited in claim 38 wherein the one or more anti-rotation tabs is raised above the viewing area.

40. The blood chamber as recited in claim 36 including an upstanding wall on the second exterior side outside of the viewing area and separating the viewing area from the shroud mating surface on the second exterior side of the blood chamber such that a well is formed around the viewing area, a floor of the well being the shroud mating surface on the second exterior side of the blood chamber.

41. The blood chamber as recited in claim 40 wherein the exterior surface of the viewing area and the shroud mating surface of the second exterior side of the blood chamber are located at substantially the same depth relative to the upstanding wall.

\* \* \* \* \*